United States Patent [19]

Dale et al.

[11] Patent Number: 5,423,806
[45] Date of Patent: Jun. 13, 1995

[54] LASER EXTRACTOR FOR AN IMPLANTED OBJECT

[75] Inventors: A. Wahlstrom Dale, Plymouth; Terrell M. Williams, Coon Rapids, both of Minn.

[73] Assignee: Medtronic, Inc., Minneapolis, Minn.

[21] Appl. No.: 131,055

[22] Filed: Oct. 1, 1993

[51] Int. Cl.⁶ .................................................. A61B 17/32
[52] U.S. Cl. .................................... 606/15; 606/7; 606/16
[58] Field of Search ............... 607/122, 126, 127, 128, 607/131; 606/7, 15, 108, 16, 1, 14

[56] References Cited

U.S. PATENT DOCUMENTS

| | | |
|---|---|---|
| 4,471,777 | 9/1984 | McCorkle, Jr. . |
| 4,574,800 | 3/1986 | Peers-Trevarton . |
| 4,576,162 | 3/1986 | McCorkle . |
| 4,582,056 | 4/1986 | McCorkle, Jr. . |
| 4,762,129 | 8/1988 | Bonzel . |
| 4,819,630 | 4/1989 | DeHart ................................ 606/15 |
| 4,834,093 | 5/1989 | Littleford et al. . |
| 4,928,695 | 5/1990 | Goldman et al. ................ 606/15 X |
| 4,943,289 | 7/1990 | Goode et al. . |
| 4,988,347 | 1/1991 | Goode et al. . |
| 4,993,412 | 2/1991 | Murphy-Chutorian . |
| 5,011,482 | 4/1991 | Goode et al. . |
| 5,013,310 | 5/1991 | Goode et al. . |
| 5,032,123 | 7/1991 | Katz et al. ............................ 606/15 |
| 5,032,123 | 7/1991 | Katz et al. . |
| 5,040,548 | 8/1991 | Yock . |
| 5,041,108 | 8/1991 | Fox et al. . |
| 5,041,109 | 8/1991 | Abela ................................... 606/15 |
| 5,061,273 | 10/1991 | Yock . |
| 5,176,674 | 1/1993 | Hofmann . |
| 5,188,632 | 2/1993 | Goldenberg . |
| 5,188,634 | 2/1993 | Hussein et al. ...................... 606/15 |
| 5,188,634 | 2/1993 | Hussein et al. . |
| 5,201,317 | 4/1993 | Kanazawa et al. ............. 606/15 X |
| 5,203,779 | 4/1993 | Muller et al. . |
| 5,207,683 | 5/1993 | Goode et al. . |
| 5,207,684 | 5/1993 | Nobles ................................ 606/108 |
| 5,254,112 | 10/1993 | Sinofsky et al. ................. 606/15 X |
| 5,263,952 | 11/1993 | Grace et al. ........................ 606/7 X |

FOREIGN PATENT DOCUMENTS

281500A7 9/1987 Germany .
9119532 12/1991 WIPO .

OTHER PUBLICATIONS

"Lead Extraction", Byrd et al., *Cardiology Clinics*, vol. 10, No. 4, Nov. 1992, pp. 735-748.
"A severed Pacemaker Lead Entrapped in a Hepatic Vein", Storm et al, *PACE*, vol. 16, Jun. 1993, pp. 1349-1353.
"Use of Laser to Extract Unwanted Pacemaker Leads", by Rao et al., Texas Heart Institute Journal, *Physics, System Design, Experimental Applications*, vol. 16, No. 3, 1989, pp. 163-168.

(List continued on next page.)

*Primary Examiner*—Peter A. Aschenbrenner
*Attorney, Agent, or Firm*—Michael J. Jaro; Harold R. Patton

[57] ABSTRACT

A lead extraction device which utilizes laser light to separate an implanted object, such as a pacemaker lead, from fibrous scar tissue and thereby permit the implanted object to be extracted from a body. The extraction device features a catheter having a central lumen. The lumen is preferably dimensioned so a pacemaker lead will fit within. The catheter is thereby guided by the lead. The catheter has at least one optical fiber to emit laser light from the distal end and thereby separate the lead from fibrous scar tissue. Disclosed embodiments include catheters which emit light parallel as well as inwardly perpendicular to the catheter and the lead. Through such catheters the lead may be separated along its length, as well as separated at its distal end from fibrous scar tissue, thereby permitting the lead to be readily extracted from the body.

26 Claims, 7 Drawing Sheets

OTHER PUBLICATIONS

"Intravascular Techniques for Extraction of Permanent Pacemaker Leads", by Byrd et al., *Journal of Thoracic and Cardiovascular Surgery*, vol. 101, No. 6, Jun. 1991, pp. 989–997.

"Migration of a Severed Transvenous Pacing Catheter and Its Successful Removal", by Ramo et al., *The American Journal of Cardiology*, vol. 22, Dec. 1968, pp. 880–884.

"Successful Removal of a Severed Transvenous Pacemake Electrode", by Gould et al., *PACE*, vol.4, Nov.–Dec. 1981, pp. 713–715.

"Experimental Study About Removal of the Implanted Tined Polyurethane Ventricular Lead by Radiofrequency Waves Through the Lead", by Ebe et al., *PACE*, vol. 14, Aug. 1991, pp. 1222–1227.

"Extraction of Implanted Transvenous Pacing Leads: A Review of a Persistent Clinical Problem", by Myers et al., *American Heart Journal*, vol. 121, No. 3, Mar. 1991, pp. 881–888.

"Removal of Chronically Implanted Pacemaker Leads", by Ikeda, *PACE*, vol. 16, Jul. 1991, p. 1537.

"Alternate Approaches to Lead Extraction", by Byrd et al., *PACE*, vol. 16, Jul. 1993, p. 1538.

"Intravascular Lead Extractions: Technique Tips and U.S. Database Results", by Sellers et al., *PACE*, vol. 16, Jul. 1993, p. 1538.

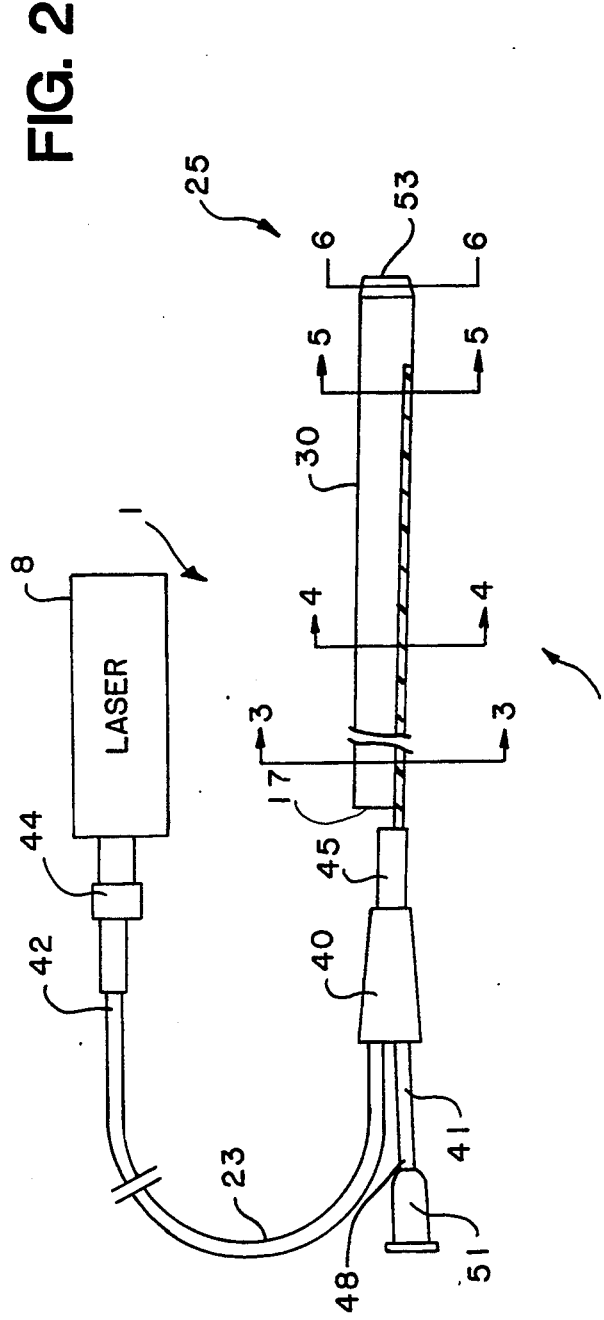
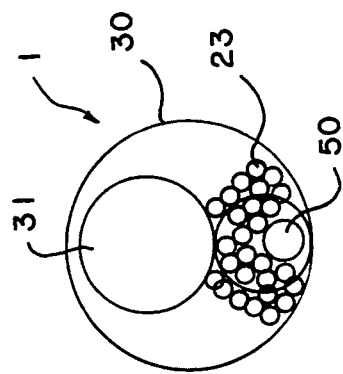
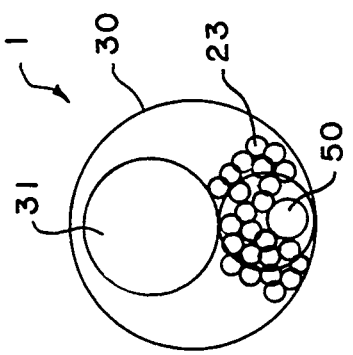
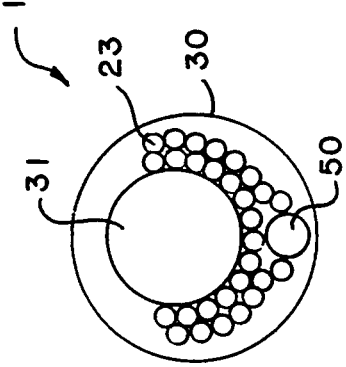

LASER EXTRACTOR FOR AN IMPLANTED OBJECT

BACKGROUND OF THE INVENTION

FIELD OF THE INVENTION

This invention relates to a method and apparatus for removal of an implanted object from a patient's body and specifically for removal of transvenous endocardial leads from a patient's heart and the venous paths thereto.

Generally speaking, a lead permits an implantable pulse generator, commonly known as a pacemaker, to stimulate the heart. More specifically an endocardial lead provides an electrical pathway between the pacemaker, connected to the proximal end of the lead, and endocardial tissue, in contact with the distal end of the lead. Endocardial tissue refers to a specific layer of tissue in the interior of the heart's chambers. In such a manner electrical pulses emitted by the pacemaker travel through the endocardial lead and stimulate the heart.

Endocardial leads are often placed in contact with the endocardial tissue by passage through a venous access, such as the subclavian vein or one of its tributaries. Thus a transvenous endocardial lead refers to a pacemaker lead which contacts endocardial tissue through a vein.

In the past, various types of transvenous endocardial leads have been introduced into different chambers of the heart including the right ventricle, right atrial appendage and atrium as well as the coronary sinus. These leads usually are composed of an insulator sleeve that contains a coiled conductor having an electrode tip attached at the distal end. The electrode tip is held in place within the trabeculations of endocardial tissue. The distal ends of many available leads include flexible tines, wedges, or finger-like projections which extend radially outward and usually are molded from and integral with the insulator sleeve of the lead. These tines allow better containment by the trabeculations of endocardial tissue and help prevent dislodgement of the lead tip.

Once an endocardial lead is implanted within a chamber, the body's reaction to its presence furthers its fixation within the heart. Specifically, shortly after placement, i.e. acute placement, a blood clot forms about the flanges or tines due to enzymes released in response to the irritation of the endocardial tissue caused by electrode tip. Over time, i.e. during chronic implantation, fibrous scar tissue eventually forms over the distal end, usually in three to six months. In addition, fibrous scar tissue often forms, in part, over the insulator sleeve within the venous system and the heart chamber. Such tissue fixes the electrode tip within the heart during the life of the lead.

Although the state of the art in implantable pulse generator or pacemaker technology and endocardial technology has advanced considerably, endocardial leads nevertheless occasionally fail, due to a variety of reasons, including insulation breaks, breakage of the inner helical coil conductor thereof and an increase in electrode resistance. Also, in some instances, it may be desirable to electronically stimulate different portions of the heart than that being stimulated with leads already in place. Due to these and other factors, therefore, a considerable number of patients may come to eventually have more than one, and sometimes as many as four or five, unused leads in their venous system and heart.

Unused transvenous leads increase the risk complications will develop. Possible complications associated with leaving unused leads in the heart and venous system include an increased likelihood an old lead may be the site of infection. Development of an infection may, in turn, lead to septicemia, a possibly fatal complication. Unused leads may also cause endocarditis. Furthermore, unused leads may entangle over time, thereby increasing the likelihood of blood clot formation. Such clots may embolize to the lung and produce severe complications or even fatality. The presence of unused leads in the venous pathway and inside the heart can also cause considerable difficulty in the positioning and attachment of new endocardial leads in the heart. Moreover, multiple leads within a vein or artery may impede blood flow causing fatigue, weakness or dizziness within the patient. Further description and detail concerning the complications associated with unused leads left in place may be found in "Lead Extraction", Byrd et al., Cardiology Clinics, Vol. 10, No. 4, November, 1992, incorporated herein by reference.

As serious as the risks associated with leaving an unused lead in place may be, the risks associated with past methods and devices for lead removal were often greater. One technique used to remove a lead was to apply traction and rotation to the outer free end of the lead. This technique, however, could only be done before the lead tip became fixed in the trabeculations of endocardial tissue by large clot development. Clot development, however, is difficult to detect. Even shortly after lead implantation there exists the risk a clot has formed. Removal of a lead at that time may cause various sized emboli to pass to the lungs, possibly producing severe complications.

In cases where the lead tip has become attached by fibrous scar tissue to the heart wall, removal of the lead has presented further major problems and risks. Porous lead tips may have an ingrowth of fibrous scar tissue attaching them to the heart wall. Sufficient traction on such leads in a removal attempt could cause disruption of the wall prior to release of the affixed lead tip, causing fatality. Even if the tines of the leads are not tightly scarred to the heart wall similar risks are faced. Moreover, lead removal may further be prevented by a channel of fibrotic scar tissue and endothelium surrounding the outer surface of the lead body and specifically the insulator sleeve, as mentioned above, at least partway along the venous pathway. Such "channel scar" tissue prevents withdrawal because of encasement of the lead. Continual strong pulling or twisting of the proximal free end of the lead could cause rupturing of the right atrial wall or right ventricular wall. Encasement by fibrous scar tissue in the venous pathway and in the trabeculations of cardiac tissue typically occurs within three to six months after the initial placement of the lead.

The great risks presented by lead removal using traction and rotation techniques are such that if it becomes imperative to remove a lead (as in the case of septicemia) those doctors who have not focused and developed a specialty in lead removal often elect to have the patient's chest opened and the lead surgically removed rather than attempt removal using traction and rotation techniques. Even those doctors who have developed a specialty in lead removal sometimes elect to have the lead surgically removed rather than face the many risks presented.

DESCRIPTION OF THE PRIOR ART

As discussed above, many of the prior methods and devices for lead removal involved the application of traction or rotation or both to the lead. U.S. Pat. No. 4,574,800 to Peers-Trevarton, incorporated herein by reference, discloses a lead extraction device constructed to fit within the central lumen of a lead conductor coil and wedge a distal portion of such device in the distal portion of the lead. Such an arrangement permits traction force to be transmitted from the proximal end of the device to the distal portion of the lead. This avoids the need to impart any substantial pulling forces along the length of the lead. As mentioned above, pulling along the lead body may result in rupture of the lead, possibly resulting in the conductor coil to unwind within a patient.

Further patents have disclosed variations on the concept of engaging the distal portion of the lead, these include: U.S. Pat. Nos. 5,207,683; 5,013,310; 4,988,347 and 4,943,289 to Goode et al., each of which is incorporated herein by reference.

The International Patent Application WO 91/19532 of Rackette, incorporated herein by reference, discloses a lead extraction device constructed to fit within the central lumen of a lead conductor coil and wedge a distal portion of such device in the distal portion of the lead. Such an arrangement permits a force to be transmitted from the proximal end of the lead extraction device to the distal portion of the lead.

In addition, other devices have featured cutting surfaces to cut through the channel scar encasing the lead body and enveloping the tine assembly. For example, U.S. Pat. Nos. 4,582,056; 4,576,162; and 4,471,777 to McCorkle, each of which is incorporated herein by reference, generally relate to lead extraction devices utilizing nesting catheters to grasp the lead and cut through, using an annular surface, such fibrous scar tissue and channel scar. U.S. Pat. No. 5,011,482 to Goode et al., incorporated herein by reference, discloses a device having a series of tubes to separate the lead from fibrotic tissue, the second tube featuring a wire at the distal end to wipe across the face of the electrode and separate it therefrom. Such devices are heavily reliant, however, upon the skill and judgement of the operator in order to consistently and reliably separate the distal tip of the lead from fibrotic scar tissue without causing injury to the patient.

Devices and techniques which rely upon traction, moreover, face a myriad of serious complications. Sustained traction to the lead, especially a lead secured by fibrous tissue at its distal end, may cause hypotension, chest: pain or avulsion. Moreover if the ventricular wall is distorted, by traction to the lead, to proximate the tricuspid valve, low cardiac output may result. Failure of the lead, and thus the heart wall, to return to its original position may cause a hemodynamic emergency. Other complications include possible myocardial rupture and tamponade as well as lead breakage.

Lead breakage is potentially very serious as rupture of the outer insulative sleeve may expose and allow conductor coil wire to uncoil. Exposed and uncoiled conductor coil wire presents a sharp and potentially very damaging surface to the cardiac and venous tissue. In such a situation full thoracic surgery is immediately required to remove the ruptured lead.

Traction may also cause the distal portion of the lead to separate from the lead body without exposing uncoiled conductor coil. Such a free floating distal portion, however, bouncing within the ventricle, may cause ventricular arrythmia, may perforate the heart and may cause vegetation to develop, itself causing emboli to be transported to the lungs.

It has been found laser light may be used to remove obstructions from within the venous system. U.S. Pat. No. 5,188,632 to Goldenberg, incorporated herein by reference, discloses a fiber optic wave guide configured to fit within at least one lumen of a catheter for performing an angioplasty. U.S. Pat. No. 5,188,634 to Hussein et al., incorporated herein by reference, discloses a catheter for ablating obstructing materials within a corporeal lumen, the catheter having an optical fiber to transmit laser energy to the site of the obstructive material. U.S. Pat. No. 5,040,548 to Yock, incorporated herein by reference, discloses a catheter having an optical fiber to transmit laser energy to the site of a venous obstruction. This device, however, requires a guide wire to be first inserted into the patient's venous system. Further patents disclosing devices utilizing laser light to remove obstructions from the blood stream include U.S. Pat. No. 5,203,779 to Muller; U.S. Pat. No. 5,176,674 to Hofman; U.S. Pat. No. 5,041,108 to Fox et al.; U.S. Pat. No. 4,993,412 to Murphy-Chutorian; U.S. Pat. No. 5,032,123 to Katz et al.; and U.S. Pat. No. 4,834,093 to Littleford, dec. et al., each of which is incorporated herein by reference.

Due to the many complications these lead removal techniques and devices face, and the efficacy of using laser light to remove obstructions from within the venous system, devices and techniques have been developed to accomplish lead removal using laser light. For example, Rao in "Use of a Laser to Extract Unwanted Pacemaker Leads", Tex. Heart Inst. J., Vol. 16, Nov. 3, 1989, incorporated herein by reference, discloses use of a laser introduced into the lumen of a coiled conductor of a lead to sever the distal portion of a lead and thereby permit removal of the lead body. The patent publication of Liebetruth et al., DD 281 500 A7, incorporated herein by reference, discloses a device similar to disclosed in the Rao publication in that it uses laser light to sever the distal portion of the lead from the lead body. Specifically a sleeve type guide cylinder having a axially movable piston to clamp along a portion of the lead is disclosed. An optical fiber which opens onto the lead where it is clamped is used to sever the lead at a position proximate the distal end.

These devices, however, are specifically designed to sever the lead so that the distal portion may be abandoned within the heart. As discussed previously, permitting a severed lead tip to remain within the body, and especially within the right ventricle may lead to serious complications such as ventricular arrythmia, heart perforation and the development of emboli. Moreover, as disclosed in the article of Storm et al. entitled "A Severed Pacemaker Lead Entrapped in a Hepatic Vein", PACE Vol. 16, June 1993, pp. 1349-1353, incorporated herein by reference, a severed lead tip may migrate through the bloodstream, possibly resulting in serious complications. Thus it is imperative that any device for lead extraction remove the entire lead and not just a portion thereof.

SUMMARY OF THE INVENTION

Thus it is an object of the present invention to remove an implanted object affixed by fibrous scar tissue in a body.

It is a further object of the present invention to remove an implanted object affixed by fibrous scar tissue in a body with a laser.

It is a still further object of the present invention to use a laser catheter which is guided by the implanted object to a location proximate the fibrous scar tissue.

In accordance with the above objects there is provided a lead extraction device which utilizes laser light to separate an implanted object, such as a pacemaker lead, from fibrous scar tissue and thereby permit the implanted object to be extracted from a body. The extraction device features a catheter having a central lumen. The lumen is preferably dimensioned so a pacemaker lead will fit within. The catheter is thereby guided by the lead. The catheter has at least one optical fiber to emit laser light from the distal end and thereby separate the lead from fibrous scar tissue. Embodiments of the present invention include catheters which emit light parallel as well as inwardly perpendicular to the catheter and the lead. Through such catheters the lead may be separated along its length, as well as separated at its distal end from fibrous scar tissue, thereby permitting the lead to be readily extracted from the body.

BRIEF DESCRIPTION OF THE DRAWINGS

FIG. 2 is a plan view of an implanted object extractor constructed in according to the present invention.

FIG. 3 is a sectional view of the device shown in FIG. 2 taken along the lines 3—3.

FIG. 4 is a sectional view of the device shown in FIG. 2 taken along the lines 4—4.

FIG. 5 is a sectional view of the device shown in FIG. 2 taken along the lines 5—5.

FIG. 6 is a sectional view of the device shown in FIG. 2 taken along the lines 6—6.

DESCRIPTION OF THE PREFERRED EMBODIMENTS

Figure 1:
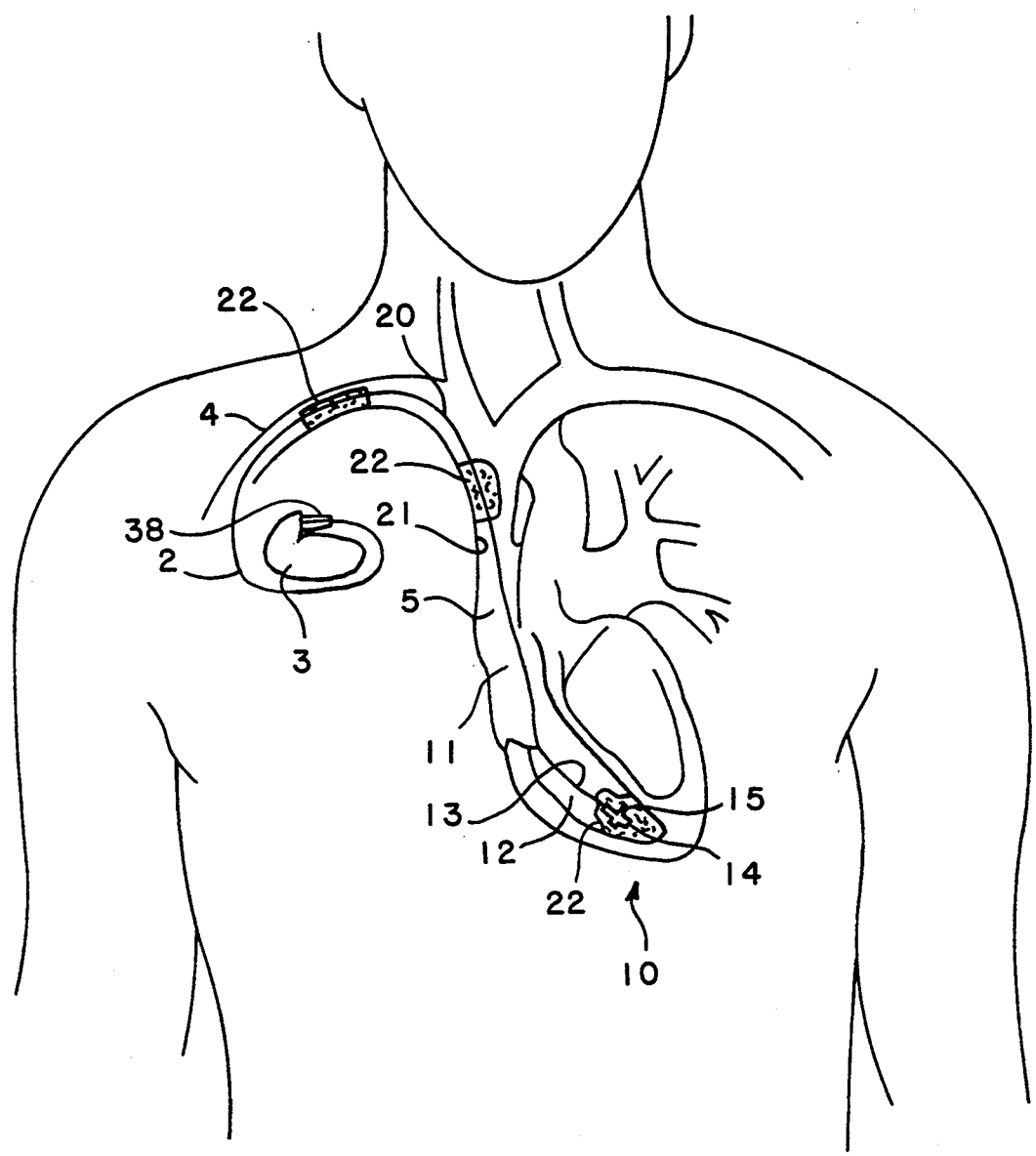
FIG. 1 is depicts a lead placed in the venous system and having its distal tip located in the heart.

Turning to the FIGS., the present invention comprises generally a catheter 1 configured to remove an implanted object from a patient's body, and especially designed to remove an implanted pacemaker lead from a patient's venous system and heart. As seen in FIG. 1 a typical transvenous endocardial lead 2 connects a pacemaker 3 to heart 10 through the right subclavian vein 4, the superior vena cava 5 and down into the heart 10. Transvenous endocardial lead 2 is shown specifically in the right ventricle 12, although leads to the right atrium 11 are often used also. Distal end 13 of lead 2 includes an electrode 14 for electrically stimulating the heart 10 and a plurality of tines 15 to provide fixation of lead 2 within heart 10. As discussed above, during chronic implantation lead 2 becomes affixed along its side surfaces 20 to inner surfaces 21 of the venous system and at its distal end 13 to heart 10 through the formation of fibrous scar tissue 22. Catheter 1 is designed to separate such fibrous scar tissue 22 from lead 2 and has a series of optical fibers 23 running throughout. Optical fibers 23 are connected at their proximal end 42 to a laser light energy source (not shown) by coupler 44 and are arranged to emit laser light energy 64 from distal end 25 of catheter 1. Catheter body 30 has a guide lumen 31 configured to permit catheter 1 to be introduced over lead 2 and be guided thereby. Specifically guide lumen 31 extends from distal end 25 of catheter 1 to proximal end 17 of catheter body 30. Catheter 1 further features stylet tube 50 to permit catheter 1 to be further guided or pushed by a stylet (not shown.) Distal end 25 of catheter 1 preferably features an annular series of optical fibers 23 which thereby provide an annular source of laser light energy about the circumference of lead 2. Through such an arrangement catheter 1 may be guided along lead 2 permitting laser light energy 64 emitted from optical fibers 23 to ablate any fibrous scar tissue 22 affixing lead 2 within the venous system and heart 10.

FIG. 2 depicts catheter 1. As seen, catheter 1 comprises catheter body 30, bifurcate cover 40 and stylet leg 41 extending therefrom, and at least one optical fiber 23. The optical fiber or fibers 23 used are preferably a 130 micron fiber available from the Spectranetics Corporation in Colorado Springs, Colo., U.S.A. The specific optical fibers used, however, are not within the scope of the claimed invention and any optical fiber suitable to transmit laser energy to ablate fibrous scar tissue may be used. Located at proximal end 42 of optical fibers 23 sits coupler 44. Coupler 44 permits optical fibers 23 to be coupled to a laser light energy source (not shown.) The laser light energy source is preferably a xenon-chloride excimer laser such as model no. CVX-300 available from the Spectranetics Corporation discussed above. Coupler 44 may be of any configuration known in the art. A suitable coupler 44 may also be obtained from Spectranetics Corporation. Bifurcate cover 40 cooperates with skirt 45 to feed optical fibers 23 into catheter body 30 as well as stylet leg 41 into stylet tube 50 in catheter body 30. Proximal end 48 of stylet leg 41 has stylet introducer 51.

Catheter body 30, as seen shown in cross section in FIGS. 3-6, has guide lumen 31 running throughout and is preferably constructed from a biocompatible material, such as polyurethane. Positioned within catheter body 30 are optical fibers 23 and stylet tube 50. Stylet tube 50 permits a stylet to be introduced through catheter body 30 and thereby move catheter 1 through the venous system. In a preferred embodiment a steerable stylet may be used with the disclosed invention, such as the steerable stylet disclosed in U.S. patent application Ser. No. 08/069,310 of Brennan et al. entitled "Steerable Stylet and Manipulative Handle Assembly" and filed May 28, 1993, incorporated herein by reference. Additionally a lead extender (not shown) may be provided to permit traction to be applied along lead throughout guide lumen 31. Specifically the lead extender would be attached to lead 2 and passed from distal end 25 of catheter 1 through guide lumen 31 and exiting at proximal end 17 of catheter body 30. Extender may be any suitable object, such as a suture or wedging stylet, which may be attached to lead and passed through guide lumen 31 to permit the application of traction to lead.

Figure 7:
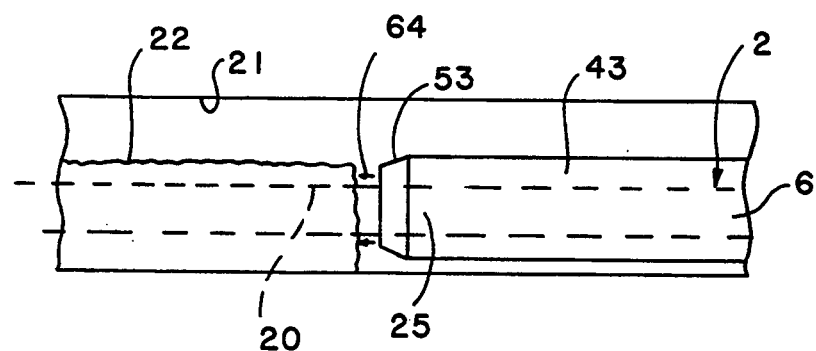
FIG. 7 is a side plan detail view of the distal portion of the implanted object extractor of FIG. 2 as it would be used to remove a lead.
Figure 9:
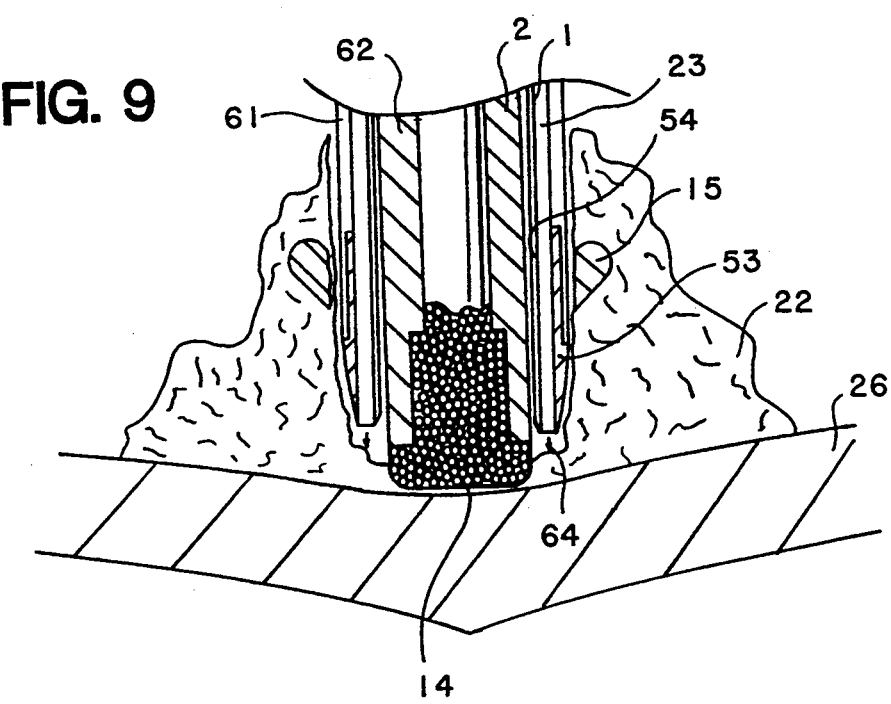
FIG. 9 is a side sectional view of the distal portion of an implanted lead showing a laser extractor for an implanted object of the present invention removing fibrous scar tissue.

As seen in FIGS. 5 and 6 optical fibers 23 are positioned within catheter body 30 so as to have an annular arrangement at distal end 25 of catheter 1. In such a fashion optical fibers 23 are arranged so as to emit laser light energy 64 onto fibrous scar tissue 22 encapsulating lead 2, specifically along body 6 of lead 2, or affixed to distal end 13 of lead 2 as seen in FIGS. 7 and 9, and ablate it. In such a fashion lead 2 may be freed and removed from a patient's body. Optical fiber may further be arranged in an annular fashion through the length of catheter body 30. In such a manner the overall diameter of catheter body 30 may be decreased, as well as the overall ability of catheter body 30 to be pushed along lead 2. Moreover, optical fibers 23 may also be incorporated as one fiber throughout catheter body 30 and separated in an annular arrangement around distal end 25.

Figure 10:
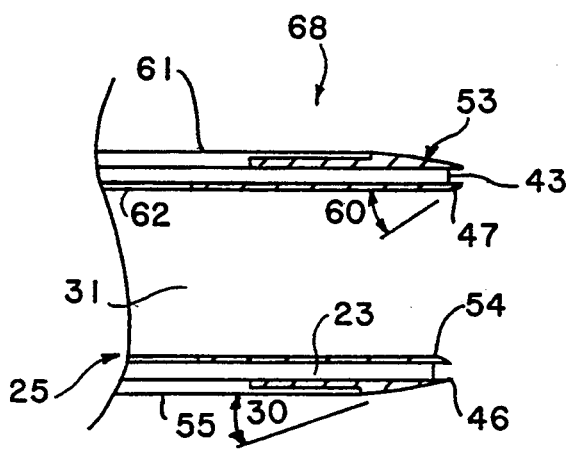
FIG. 10 is a side sectional view of the distal portion a laser extractor for an implanted object of the present invention.

Detail of distal end 25 of catheter 1 is shown in FIG. 10. As seen distal end 25 of catheter 1 features a guard assembly 68. Guard assembly 68 is constructed from outer jacket 61 and inner sleeve 62. Specifically the distal end 43 of each optical fiber 23 is sandwiched between guard band 53 and guard ring 54. Guard band 53 is preferably made from a platinum iridium alloy and preferably has an outer taper 55 of 30 to 60 degrees. Guard ring 54 is preferably made from stainless steel and preferably has an inner taper 60 of 30 of 60 degrees. Distal end 43 of optical fibers 23 are recessed, preferably 1 millimeter, from distal end 46 of guard band 53 and distal end 47 of guard ring 54, as best seen in FIG. 10. Through the guard assembly 68 photo degradation of lead 2 from laser light energy 64 emitted from optical fibers 23 is minimized. This is important because if the lead insulation is ablated away, the coiled conductor typically used in an endocardial lead could become exposed and possibly unwind. As detailed above such a situation is undesirable. This feature further minimizes the possible emission of by-products from the photo degradation of lead, and in particular by-products from the photo degradation of lead insulation, into the blood stream. Guard band 53 and guard ring 54, because they are constructed from radiopaque materials, also provide a convenient marker of the position of distal end 25 of catheter 1 when using a fluoroscope. Outer jacket 61 and inner sleeve 62 are preferably made from a biocompatible material, such as polyurethane. Outer jacket 61 and inner sleeve 62 may further be formed integral with catheter body 30.

Figure 11:
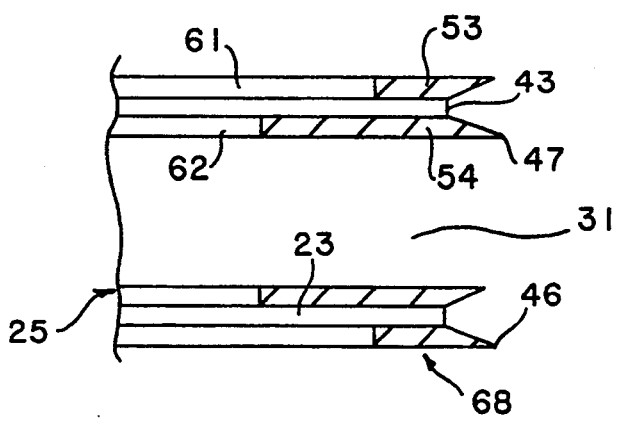
FIG. 11 is a side sectional view of the distal portion of an alternate embodiment of a laser extractor for an implanted object of the present invention.

A further embodiment of a distal end 25 of catheter 1 is shown in FIG. 11. This embodiment is substantially the same as that shown in FIG. 10 but for the reverse outer taper 55 at distal end 46 of guard band 53 and reverse inner taper 60 at distal end 47 of guard ring 54. Through such a configuration it is believed that as catheter 1 contacts fibrous scar tissue or channel scar along body 6 of lead 2, reverse tapers 55, 60 function to direct or plow such tissue toward distal end 43 of optical fibers 23 and thereby be ablated by the laser light energy 64.

Figure 12:
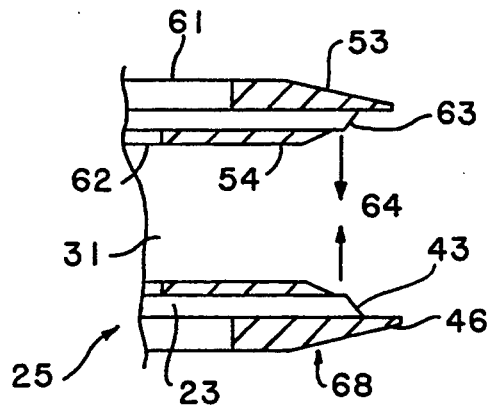
FIG. 12 is a side sectional view of the distal portion of an alternate embodiment of a laser extractor for an implanted object of the present invention.

A further embodiment of a distal end 25 of catheter 1 is shown in FIG. 12. This embodiment is substantially the same as that shown in FIG. 10 but for bevelled surface 63 along distal end 43 of optical fibers 23. Through bevelled surface 63 laser light energy 64 is emitted from optical fibers 23 in a direction other than parallel to distal end 25 of catheter 1. As seen bevelled surface 63 depicted in FIG. 11 causes laser light energy, shown by arrows 64 to be emitted towards the center of guide lumen 31 of catheter 1. Such an emission of light is especially useful to free distal end 13 of lead 2 affixed by fibrous scar tissue 22 as seen in FIGS. 13 and 14.

Figure 13:
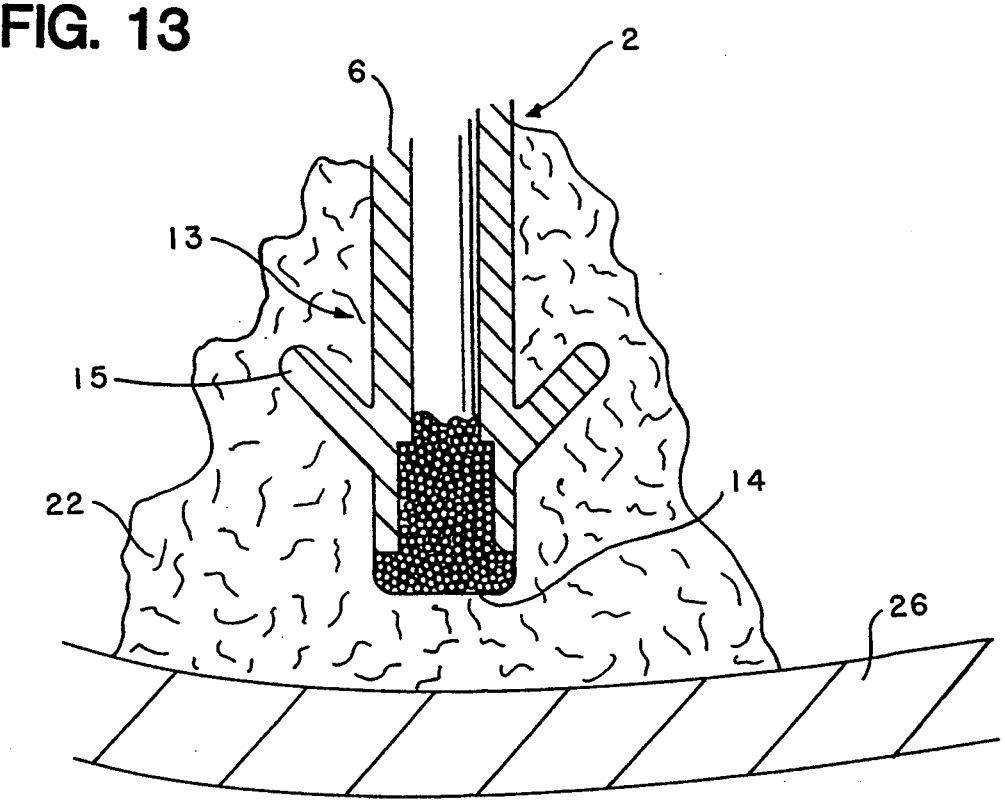
FIG. 13 is a side sectional view of the distal portion of an implanted lead showing the formation of fibrous scar tissue separating the electrode tip from direct contact with heart tissue.
Figure 14:
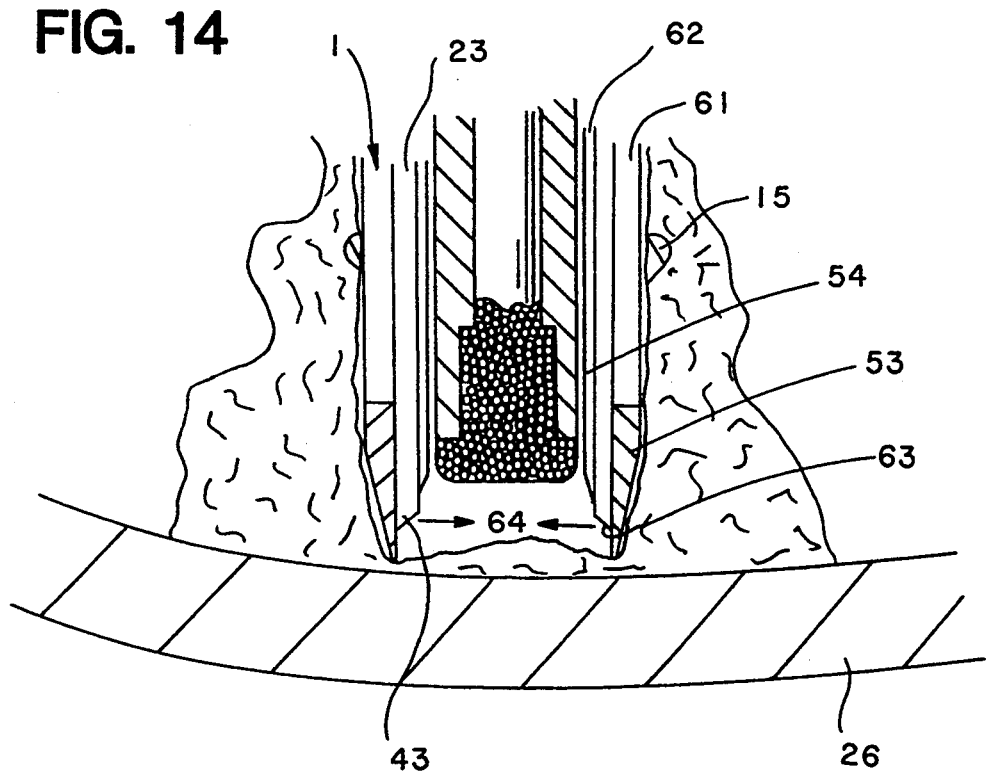
FIG. 14 is a side sectional view of the distal portion of an implanted lead showing an alternate embodiment of a laser extractor for an implanted object of the present invention removing fibrous scar tissue.

As seen in FIG. 13, lead 2 is affixed by fibrous scar tissue 22 away from heart tissue 26. Through a catheter 1 having bevelled surface 63 along distal end 43 of optical fibers 23, as seen in FIG. 14, fibrous scar tissue 22 proximate distal end 13 of lead 2 and especially along the face of electrode 14 may be ablated thereby completely freeing lead 2.

Figure 16:
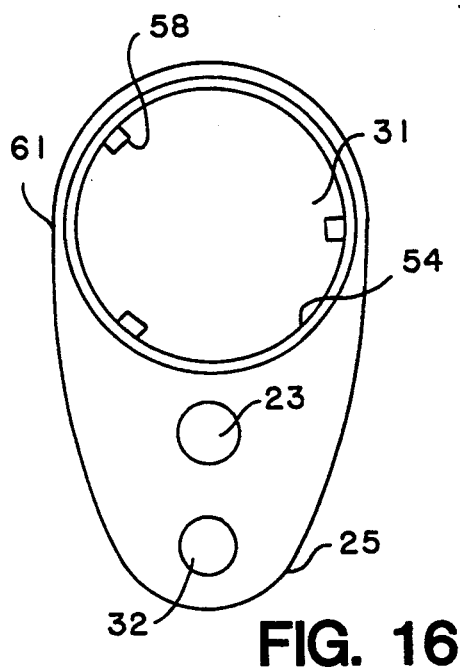
FIG. 16 is a detail of the distal end of an alternative embodiment of a laser extractor for an implanted object of the present invention.
Figure 17:
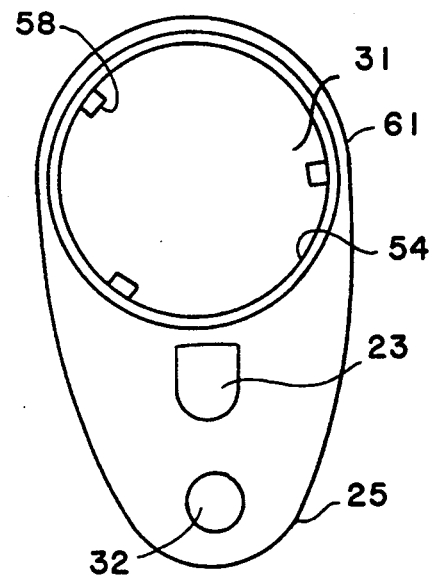
FIG. 17 is a detail of the distal end of an alternative embodiment of a laser extractor for an implanted object of the present invention.
Figure 19:
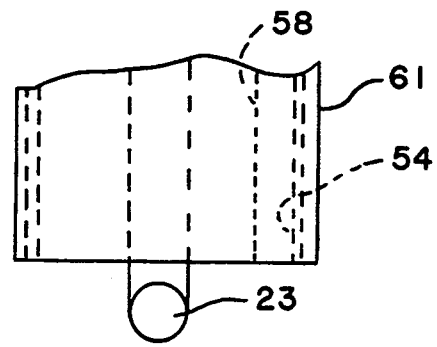
FIG. 19 is a detail of a cross-sectional view of an alternative embodiment of a laser extractor for an implanted object of the present invention.
Figure 8:
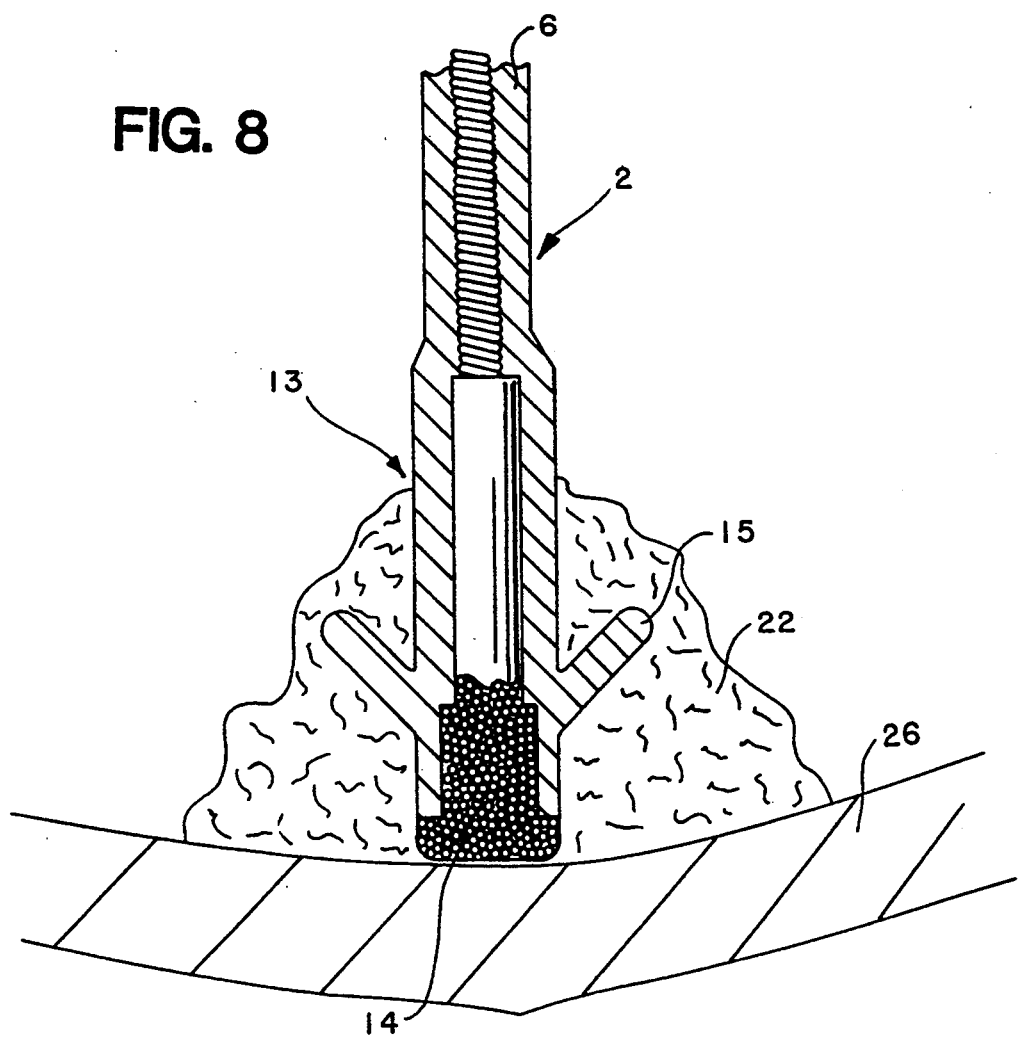
FIG. 8 is a side sectional view of the distal portion of an implanted lead showing the formation of fibrous scar tissue.
Figure 15:
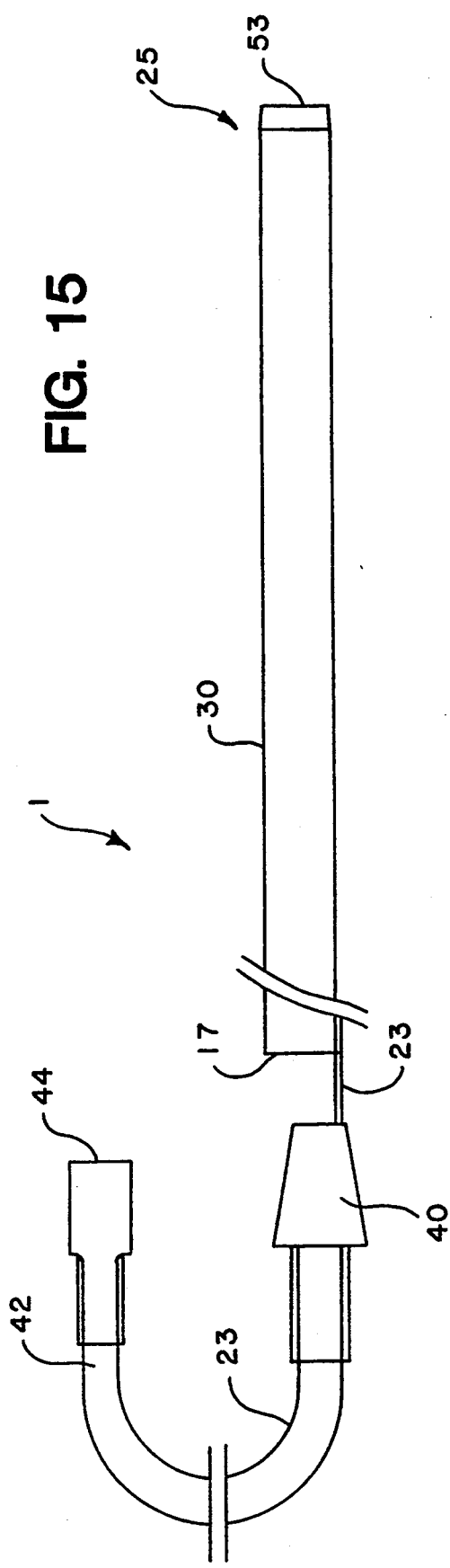
FIG. 15 is a plan view of an alternate embodiment of a laser extractor for an implanted object of the present invention.

A further embodiment of the catheter 1 is shown in FIG. 15. As seen this embodiment is substantially similar to that shown in FIG. 2 with the exception it does not feature stylet introducer 51, stylet leg 41 or stylet tube Still further embodiments of catheter 1 are shown in FIGS. 16 and 17. The embodiment depicted in FIG. 16 is substantially similar to those previously described with the exception of utilizing only a single optical fiber 23 and distal end 25 having an asymmetrical cross section. The embodiment depicted in FIG. 17 is similar to that shown in FIG. 16 with the exception that optical fiber 23 is curved at its distal end, as best viewed in FIG. 19. These embodiments, because only a single optical fiber is used, allow precise and controlled ablation of fibrous scar tissue 22 affixing lead 2, especially in conjunction with a stylet located in stylet tube 50 used to rotate catheter 1 about lead 2. Furthermore means may be provided to manipulate optical fiber 23, such as that disclosed in the U.S. Pat. No. 5,203,779 and U.S. Pat. No. 5,041,108, each incorporated herein by reference.

Figure 18:
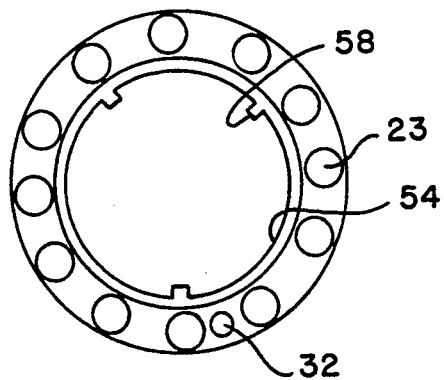
FIG. 18 is a detail of a cross-sectional view of an alternative embodiment of a laser extractor for an implanted object of the present invention.

Each of the embodiments discussed above may further feature a series of centering tabs 58 within the lumen of the catheter 1, preferably near the distal end. These centering tabs 58 may be best seen in FIG. 18.

Tabs 58 assist in avoiding the inadvertent vaporization of lead 6 by the emitted laser light energy 64. Other devices, such as a series of leaf springs longitudinally aligned with catheter 1 may also be used.

Operation of catheter 1 to extract an implanted object, and specifically a lead 2, is as follows. The proximal end of lead 2 is uncovered surgically so that catheter 1 may be introduced over it. Next proximal end of lead 2 is introduced into guide lumen 31. If needed, this may be accomplished by removing the connector pin assembly 38 from proximal end of lead 2, affixing an extender which extends throughout guide lumen 31 to the lead 2, as discussed above, and through traction along extender, introducing lead 2 within guide lumen 31. Once catheter 1 is positioned so lead 2 extends through guide lumen 31, catheter 1 is moved until distal end 25 of catheter 1 is proximate fibrous scar tissue 22. As represented in FIG. 7, laser light energy 64 from a laser (not shown) is transmitted through optical fibers 23 and onto fibrous scar tissue 22, thereby ablating fibrous scar tissue 22 and releasing lead 2 in the area proximate distal end 25 of catheter 1. Catheter 1 is repositioned until once again distal end 25 of catheter 1 is proximate fibrous scar tissue 22. Transmission of laser light energy 64 onto fibrous scar tissue 22 is repeated along the entire length of lead 2 until lead 2 is no longer affixed by fibrous scar tissue 22 along its side surface 20. As seen in FIG. 9 laser light energy 64, besides ablating fibrous scar tissue 22., also ablates and cuts through tines 15, particularly if tines 15 are constructed from common lead materials, such as silicone or polyurethane.

Once side surface 20 of lead 2 is released from fibrous scar tissue 22, only fibrous scar tissue proximate distal end 13 of lead 2 at distal face of electrode 14 retains lead, as shown in FIG. 9. At this point traction may be applied to either proximal end of lead 2 or to a point proximal distal end of lead 2, such as through a snagging stylet as disclosed in U.S. Pat. Nos. 5,207,683; 5,013,310; 4,988,347 and 4,943,289 to Goode et al. to withdraw lead 2 from fibrous scar tissue 22 and thereby accomplish lead 2 removal. Use may also be made of a sheath, such as that disclosed in U.S. Pat. No. 5,011,482 to Goode et al., to overlay lead 2 during traction and apply counter traction at a site near the electrode to confine the traction force to an area within the sheath.

In addition, catheter 1 as shown in FIG. 12 having inwardly projecting laser light energy 64 may also be used to completely free distal end 13 of lead 2. Specifically this embodiment is positioned along lead 2 as shown in FIG. 14 such that laser light energy 64 emitted by bevelled surfaces 63 of optical fibers 23 separates lead 2 as shown.

While the embodiments of the present invention have been described in particular application to a laser extractor for a cardiac lead, it will also be understood the invention may be practiced to remove other implanted objects, including but not limited to such other implanted objects as stents. Moreover, although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A device for removing an object from the venous system comprising:
    an elongated catheter having a distal end and a proximal end, said catheter having a tubular portion;
    a lumen in said catheter so that said object may be introduced into said lumen;
    at least one optical fiber supported by said tubular portion, said optical fiber extending to a region proximate said distal end of said catheter, said distal end having a guard assembly, said guard assembly comprising a guard band positioned about an exterior surface of said elongated catheter and a guard ring positioned about an interior surface of said elongated catheter, said optical fiber extending between said guard band and said guard ring, said optical fiber having a distal end, said guard assembly having a distal end, said optical fiber distal end is spaced proximally from said guard assembly distal end; and
    a source of laser energy communicating with said optical fiber so that said light energy will be transmitted to said region proximate said distal end of said catheter.

2. The device of claim 1 further comprising a stylet port in said catheter to permit a stylet to be mated with said catheter.

3. The device of claim 1 further comprising said optical fiber extending to said region proximate said distal end in a direction parallel with said catheter.

4. The device of claim 1 further comprising said optical fiber extending to said region proximate said distal end in a first direction relative to said catheter.

5. The device of claim 4 wherein said first direction being towards said lumen of said catheter.

6. The device of claim 4 further comprising a guard band at said distal end of said catheter, said guard band positioned in the path of laser energy emitted in said first direction.

7. The device of claim 1 further comprising said catheter is rotatable about said object.

8. The device of claim 1 further comprising said distal end of said catheter is rotatable about said object.

9. The device of claim 1 further comprising said distal end of said catheter being radiopaque.

10. A method for removing an implanted object affixed to a body by fibrous scar tissue comprising the steps of:
    introducing a catheter having a lumen and at least one optical fiber into said venous system, said catheter further having a distal end having a guard assembly, said guard assembly comprising a guard band positioned about an exterior surface of said catheter and a guard ring positioned about an interior surface of said catheter, said optical fiber having a distal end, said guard assembly having a distal end, said optical fiber distal end is spaced proximally from said guard assembly distal end;
    positioning said implanted object within said lumen of said catheter;
    positioning said distal end of said catheter proximate said fibrous scar tissue;
    transmitting laser energy through said optical fiber to said fibrous scar tissue immediately adjacent said distal end; and
    removing said object from said venous system.

11. A method for removing an implanted object affixed by fibrous scar tissue in a body comprising the steps of:

providing a catheter body having a tubular portion supporting at least one optical fiber, said optical fiber having a distal end, said catheter body having a lumen therethrough, said catheter further having a distal end having a guard assembly, said guard assembly comprising a guard band positioned about an exterior surface of said catheter and a guard ring positioned about an interior surface of said catheter, said guard band having a distal end, said optical fiber distal end is spaced proximally from said guard band distal end;

placing the catheter body around said implanted object;

moving said catheter body along said implanted object until a distal end of said catheter body is positioned adjacent fibrous scar tissue which affixes said implanted object;

energizing a laser connected to said optical fiber to cause laser energy to be emitted into said fibrous scar tissue immediately adjacent said distal end;

moving the catheter body along said implanted object as the fibrous scar tissue releases said implanted object; and removing said implanted object from said venous system.

12. The method of claim 11 wherein said lumen is centrally located with respect to said catheter body.

13. The method of claim 11 further comprising the step of centering said implanted object within said lumen.

14. The method of claim 12 wherein said centering step comprises providing a series of springs along an interior surface along said lumen.

15. The method of claim 13 wherein said centering step comprises providing a series of centering tabs along an interior surface along said lumen.

16. The method of claim 11 further comprising the step of providing a stylet lumen in said catheter body.

17. The method of claim 16 further comprising the step of providing a steerable stylet within said stylet lumen.

18. The method of claim 11 further comprising the step of steering said catheter body along said implanted object.

19. The method of claim 11 further comprising the step of providing an optical fiber which emits laser energy parallel to said catheter body.

20. The method of claim 11 further comprising the step of providing an optical fiber which emits laser energy away from said implanted object.

21. The method of claim 11 further comprising the step of rotating said catheter body.

22. The method of claim 11 further comprising the step of rotating said optical fiber.

23. The method of claim 11 further comprising the step of providing an optical fiber which emits laser energy towards said implanted object.

24. The method of claim 11 wherein said implanted object is a pacemaker lead.

25. The device of claim 1 wherein said guard ring has a distal end, said distal end has a taper.

26. The device of claim I wherein said guard band has a distal end, said distal end has a taper.

* * * * *